United States Patent [19]

Piscopo et al.

[11] Patent Number: 5,469,861
[45] Date of Patent: Nov. 28, 1995

[54] POSTURE MONITOR

[75] Inventors: Mark F. Piscopo, 59 Macintosh Rd., Bedford, N.H. 03110; Bruce E. Stetson; Nancy E. Stetson, both of Goffstown, N.H.

[73] Assignee: Mark F. Piscopo, Bedford, N.H.

[21] Appl. No.: 300,594

[22] Filed: Sep. 2, 1994

Related U.S. Application Data

[63] Continuation of Ser. No. 956,117, Oct. 5, 1992, abandoned, which is a continuation-in-part of Ser. No. 870,064, Apr. 17, 1992, abandoned.

[51] Int. Cl.$^6$ ................................................... A61B 5/103
[52] U.S. Cl. ............................ 128/781; 128/782; 340/573
[58] Field of Search ........................... 128/774, 782, 128/781; 340/573, 575; 342/458

[56] References Cited

U.S. PATENT DOCUMENTS

| | | | |
|---|---|---|---|
| 2,532,915 | 12/1950 | Horner | 128/2 |
| 2,560,289 | 7/1951 | Hasbrook | 343/13 |
| 3,608,541 | 9/1971 | Leland | 128/2 |
| 3,911,899 | 10/1975 | Hattes | 128/2 |
| 4,007,733 | 2/1977 | Celeste et al. | 128/2 |
| 4,055,168 | 10/1977 | Miller et al. | 128/2 |
| 4,493,328 | 1/1985 | Saito | 128/782 |
| 4,527,982 | 7/1985 | Salzman | 434/258 |
| 4,660,829 | 4/1987 | Witeneir | 273/29 |
| 4,688,037 | 8/1987 | Krieg | 340/825 |
| 4,730,625 | 3/1988 | Fraser et al. | 128/781 |
| 4,800,897 | 1/1989 | Nilsson | 128/782 |
| 4,905,207 | 2/1990 | Fellinger et al. | 367/99 |
| 5,012,819 | 5/1991 | Marras | 128/781 |
| 5,029,194 | 7/1991 | Young et al. | 378/89 |
| 5,038,137 | 8/1991 | Lloyd | 340/573 |
| 5,153,584 | 10/1992 | Engira | 340/870.18 |
| 5,170,172 | 12/1992 | Weinstein | 342/458 |

FOREIGN PATENT DOCUMENTS

| | | | |
|---|---|---|---|
| 2228869 | 9/1990 | United Kingdom | 128/781 |
| 9007360 | 6/1990 | WIPO | 128/781 |

Primary Examiner—Stephen C. Pellegrino
Assistant Examiner—Guy V. Tucker
Attorney, Agent, or Firm—Hamilton, Brook, Smith & Reynolds

[57] ABSTRACT

A method and apparatus for monitoring posture are disclosed. A first unit is attached to a first position on a user's body, and a second unit is attached to a second position on the user's body. A signal such as an ultrasonic signal is transmitted by the first unit to the second unit. In response, the second unit transmits a signal back to the first unit. The round-trip travel time of the signals is proportional to the distance between the units. If the distance differs from an ideal distance by more than a maximum allowable amount, improper posture is indicated to the user by an alarm signal.

18 Claims, 6 Drawing Sheets

POSTURE MONITOR

This application is a continuation of application Ser. No. 07/956,117 filed Oct. 5, 1992, now abandoned, which is a continuation-in-part of application Ser. No. 07/870,064 filed Apr. 17, 1992, now abandoned.

BACKGROUND

The importance of correct posture for both health and aesthetic reasons has long been appreciated. One application in which correct posture is particularly important is during treatment of neck and back injuries such as whiplash. Such injuries usually require lengthy programs of treatment and therapy. The success of this treatment can depend a great deal on the patient maintaining proper posture at all times. Poor posture can impede the progress of the therapy.

To assist patients in maintaining proper posture, numerous posture training devices have been developed. Most of these devices involve mechanical braces to hold the patient in the correct position. Others provide some form of feedback to the user to inform him that his posture is not correct. These warning devices involve linking two parts of the body by some mechanical means. An increase or decrease in tension in such a mechanical linkage beyond specified limits indicates improper posture.

A need remains however to provide a non-intrusive, precise and dependable system to monitor and correct posture while at the same time reducing the cost and length of treatment and therapy.

SUMMARY OF THE INVENTION

The present invention provides an apparatus and a method for monitoring posture. A first or master unit is placed in a substantially fixed relation to a first position on the body of a person. A second or slave unit is placed in a substantially fixed relation to a second position on the body. A sensor is used to sense a signal that is correlated with the distance between the master unit and the slave unit.

In one embodiment, the master unit is fixed to the person's waist, and the slave unit is fixed to the person's neck. Signals such as ultrasonic signals are transmitted back and forth between the master and slave units. The time of travel of the signals is proportional to the distance between the units. Therefore, a measurement of this travel or propagation time indicates distance between the units, which in turn indicates whether the person's posture is correct.

In a preferred embodiment, both the master and slave units comprise ultrasonic transmit and receive circuitry. The master unit generates an ultrasonic signal and transmits it via its transmit circuitry to the slave unit. The slave unit receives the signal via its receive circuitry and responds by generating a second signal. The slave unit then transmits the second signal via its transmit circuitry to the master unit. The master unit receives the second signal via its receive circuitry. The time between transmission of the first signal and reception of the second signal by the master unit is recorded. That time is compared to an ideal time pre-set by the user via a calibration function of the monitor. The difference in the two times is correlated to the deviation of the distance between the units from the ideal distance set by the user during calibration.

If the differential distance is more than a predetermined maximum allowable deviation, an alarm signal is generated. That alarm can be an audible beeper or a within the master unit in contact with the user's body or some other mechanism informing the wearer that maximum selected deviation has occurred. In this preferred embodiment, the type of alarm is selectable via an alarm select switch on the master unit.

In another embodiment an alarm is not issued when posture is incorrect. Rather, posture measurements are recorded in a memory. These measurements may be read from the memory at any time to obtain a user's posture history.

In another embodiment, the master unit transmits a signal which reflects off the slave unit and returns to the master unit. The round-trip travel time of the signal is sensed by the sensor and the distance between the units is thus indicated.

In another embodiment, the master unit transmits a signal to the slave unit. This signal indicates the time the signal was transmitted. The time is indicated by encoded time information in the signal. By decoding the time of transmission and comparing it to the time of reception, the travel time can be determined by the slave unit. This indicates the distance between the units.

In another embodiment, the master unit transmits a signal of known power level to the slave unit. Since the power level of the signal decreases over the distance between the units, the power level of the received signal is indicative of the distance between the units. The slave unit measures the power level of the received signal and compares it to a pre-set level which indicates correct posture.

In another embodiment, a sensor external to both units monitors the signals transmitted back and forth between the units. The travel time of the signals is used by the sensor to determine the distance between the units.

The signals used in the invention can be acoustic, and specifically ultrasonic, or they can be electronic, magnetic, or electromagnetic.

In one embodiment, each of the master and slave units comprises a control circuit such as a microcontroller or a microprocessor. The control circuit may be an application-specific integrated circuit (ASIC). In an alternative embodiment, only the master unit comprises a control circuit. The control circuit controls the transmit and receive circuitry as well as most of the other functions of the monitor. These functions include a calibrate function which allows the user to set and store the ideal distance between master and slave units when his or her posture is correct. This is accomplished by the user standing or sitting in a known proper position and pressing a calibrate switch on the master unit. A pause function is also provided to allow the user to inhibit the alarm. An alarm select function allows the user to choose between the audible alarm and the vibrator alarm. A position select function provides the monitor with the capability of monitoring standing or sitting posture. The user selects the correct position to be monitored via a position select switch on the master unit.

When monitoring posture, the posture monitor transmits signals back and forth between the master and slave units at a given sample rate. In the preferred embodiment, this sample rate is selectable by the user.

In another embodiment, the monitor has a channel select function which allows a choice of one of eight signal channels to prevent interference with other monitors. The signals transmitted between the units are encoded with one of eight possible codes. Thus, as many as eight monitor units may be operated in one localized area without interference. Also, a delay is provided between the time improper posture is sensed and initiation of an alarm. This allows the monitor to distinguish between brief harmless movements of the user and a truly improper body position.

The posture monitor of the present invention provides distinct advantages over prior devices. The prior devices relied on some form of mechanical linkage between parts on the body. A strap or harness or cord was usually stretched between fixed points on the body. An increase or decrease in tension in the linkage caused a motion in the linkage which could be sensed by some electro-mechanical means at an end of the linkage. These devices were prone to the inaccuracies inherent in any mechanical system. Uncontrollable mechanical effects such as friction, mechanism backlash and the like introduced these inaccuracies into the systems. Undesirable results were also induced by the unpredictably complex motions of the human body.

Motions which are not related to improper posture, such as a simple shrug of the shoulders, were not isolated from those which indicated a problem. A posture problem was indicated where a user made a common natural movement. The electronic monitor of the present invention provides much more accurate monitoring. By precisely measuring signal travel times with the control circuit and associated circuits, a high degree of accuracy is obtained. Mechanical inaccuracies present in prior systems are virtually eliminated. Also, an alarm delay provided by the present invention substantially reduces or eliminates activations by inconsequential body movements. Only improper posture positions extending longer than a selected time interval cause activations. The use of a processing circuitry provides the present invention with a great deal of versatility. The calibrate function allows the monitor to be set to function on any user. The position select function enables monitoring of proper sitting and standing postures. The user may pause the monitor operation when he knows he will be assuming a position which will cause an activation of the alarm. The processing circuitry also allows the encoding of the transmitted signals to allow more than one monitor to operate simultaneously in the same area.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
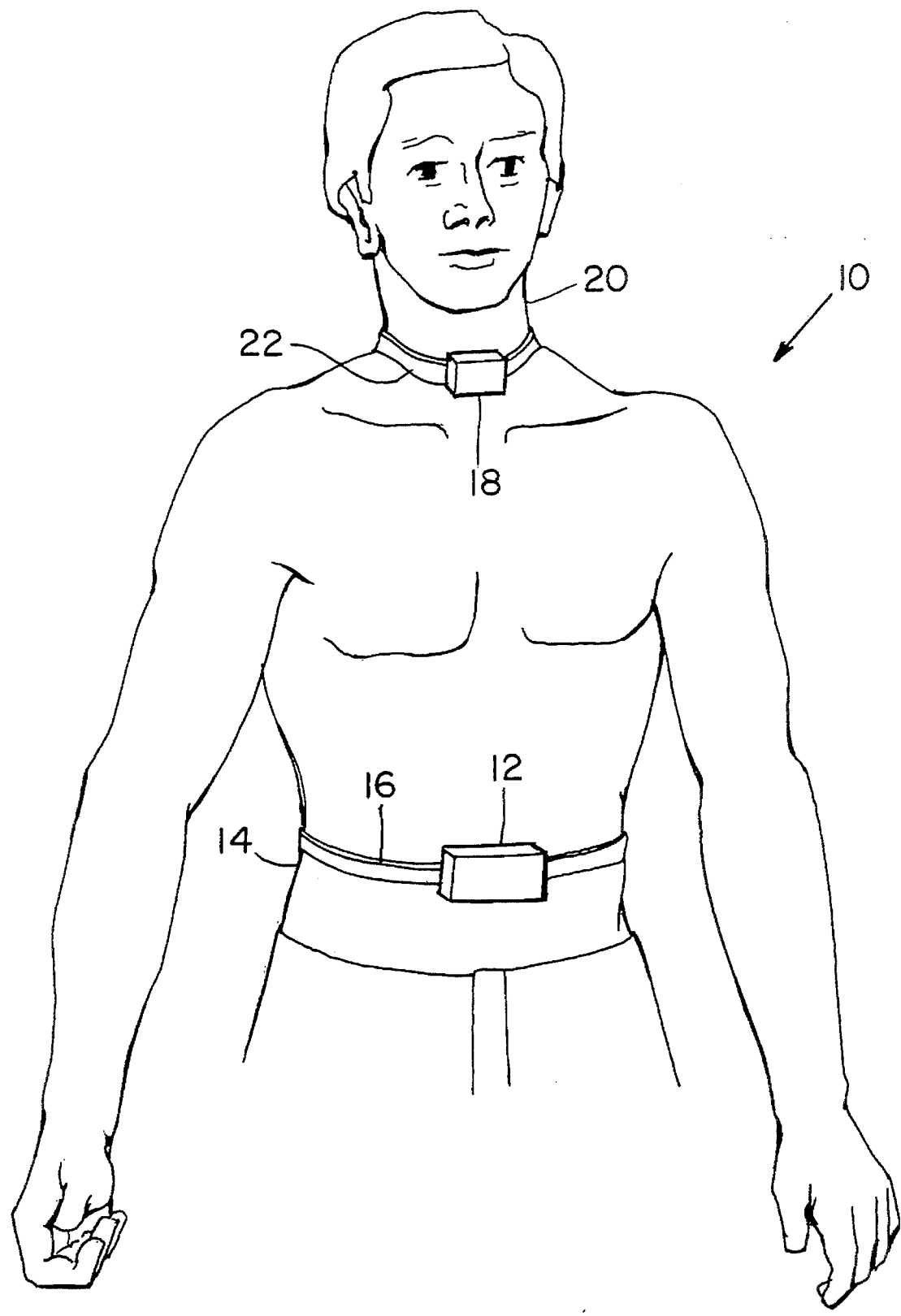
FIG. 1 is a view of a person with an embodiment of the posture monitor of the present invention attached to his body.

A preferred embodiment is illustrated in FIG. 1 which depicts a user with the posture monitor 10 of the present invention attached to his body. The master unit 12 is shown attached to the user's waist 14 by belt 16. The slave unit 18 is shown attached to the user's neck 20 by strap 22. The user is in a normal standing position with proper posture. From FIG. 1 it can be seen that if the user slouches or otherwise assumes a position of improper posture, the distance between the units 12 and 18 will change. This change in distance will be sensed by the monitor 10, and an alarm will be issued to inform the user.

Figure 2:
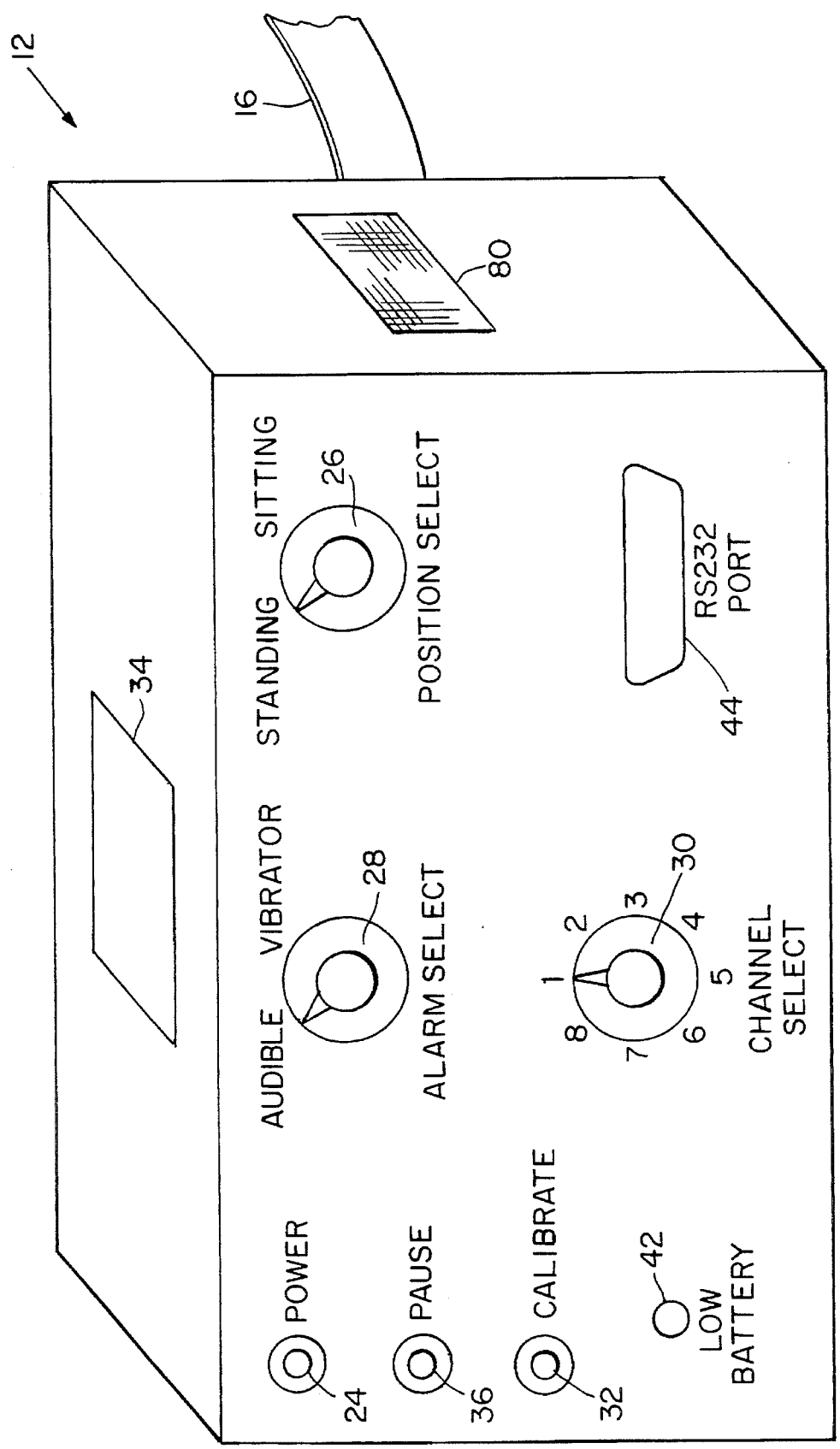
FIG. 2 is a schematic illustration of the master unit of the preferred embodiment of the posture monitor.

FIG. 2 schematically depicts the master unit 12 of the posture monitor 10. Before monitoring begins, the master unit 12 is attached snugly to the user's waist 14 by belt 16. To begin monitoring, the user applies power to the unit 12 by activating power switch 24. Next, the user provides an input to the unit 12 based on whether he will be standing or sitting during monitoring. This is accomplished by setting the position select switch 26 to the proper position. The user can select the type of alarm signal desired by setting the alarm select switch 28 to the desired position. With the alarm select switch 28 in the "audible" position, alarm activations will be issued via beeper 80 in the master unit 12. If the switch 28 is set to "vibrator" the vibrator 82 in the master unit (not shown) will be activated. The vibrator 82 is located within the master unit 12 and is exposed to the body of the person wearing the master unit 12. When a vibrator alarm is issued, the user can feel the slight vibration issued by the vibrator 82.

Next, the user can select a sample interval by setting the sample rate switch 30 to one of the two possible positions. When the switch 30 is in the "3" position, a pulse is transmitted from the master unit to the slave unit approximately every three seconds. A four second interval can also be selected. Because of the short duration of a pulse (approximately 15 msec) and the relatively long duration between pulses, two monitors operating in the same area will virtually never interfere with each other.

Finally, the user calibrates the monitor 10 by assuming a proper posture and pressing and releasing the calibrate switch 32. In response, the master unit 12 transmits an ultrasonic signal to the slave unit 18 (not shown) via the ultrasonic transducer 34. When the slave unit 18 receives the signal, it will transmit a second signal back to the ultrasonic transducer 34 of the master unit 12. The time between the transmission of the first signal and reception of the second signal by the master unit 12 is measured and stored in the circuitry of the master unit 12 as a reference time to be used during subsequent posture monitoring.

During monitoring, the master unit 12 transmits signals to the slave unit 18 and receives return signals from the slave unit 18 in much the same fashion as it does during calibration. Each round trip time is recorded and compared with the time stored during calibration by a comparator circuit. The difference in time corresponds to the amount that the distance between units 12 and 18 differs from the calibrated distance. In a preferred embodiment, the maximum allowable differential distance is 0.25 inch. The sampling sequence is repeated at the rate selected by the sample rate switch 30. If three consecutive samples are outside the allowed distance, an alarm is issued. The type of alarm issued depends upon the setting chosen by the user on the alarm select switch 28.

The requirement of three consecutive samples outside allowed limits provides the posture monitor with a delay feature. The delay feature eliminates alarm activations caused by brief movements of the user which cause the distance between units 12 and 18 to change by more than the pre-set tolerance. Once the user assumes a position of bad posture, he must maintain that position for the delay time before he will receive an alarm. Within that time, he may correct his posture without being warned by the monitor 10.

While the monitoring function 10 is active, the user may wish to temporarily assume a position which he knows will cause an alarm activation. During this time it may be inconvenient or undesirable for an alarm to issue, and so the user may wish to disable the alarm. This is accomplished in the present invention via the pause function. To disable the alarm, the user simply presses and releases the pause button 36 on the master unit 12. Until the button 36 is pressed and released again, all alarms are inhibited. While the pause function is active, no monitoring is performed. When the user resumes his normal position, he presses and releases the pause button 36 and normal monitoring operation continues.

The posture monitor 10 is powered by batteries. The master unit 12 is powered by battery 38 (see FIG. 3), and the slave unit 18 is powered by battery 40 (see FIG. 4a). The master unit 12 has a low battery indicator LED 42 (see FIG. 2) which lights when batteries 38 in the master unit 12 need replacement.

Figure 3:
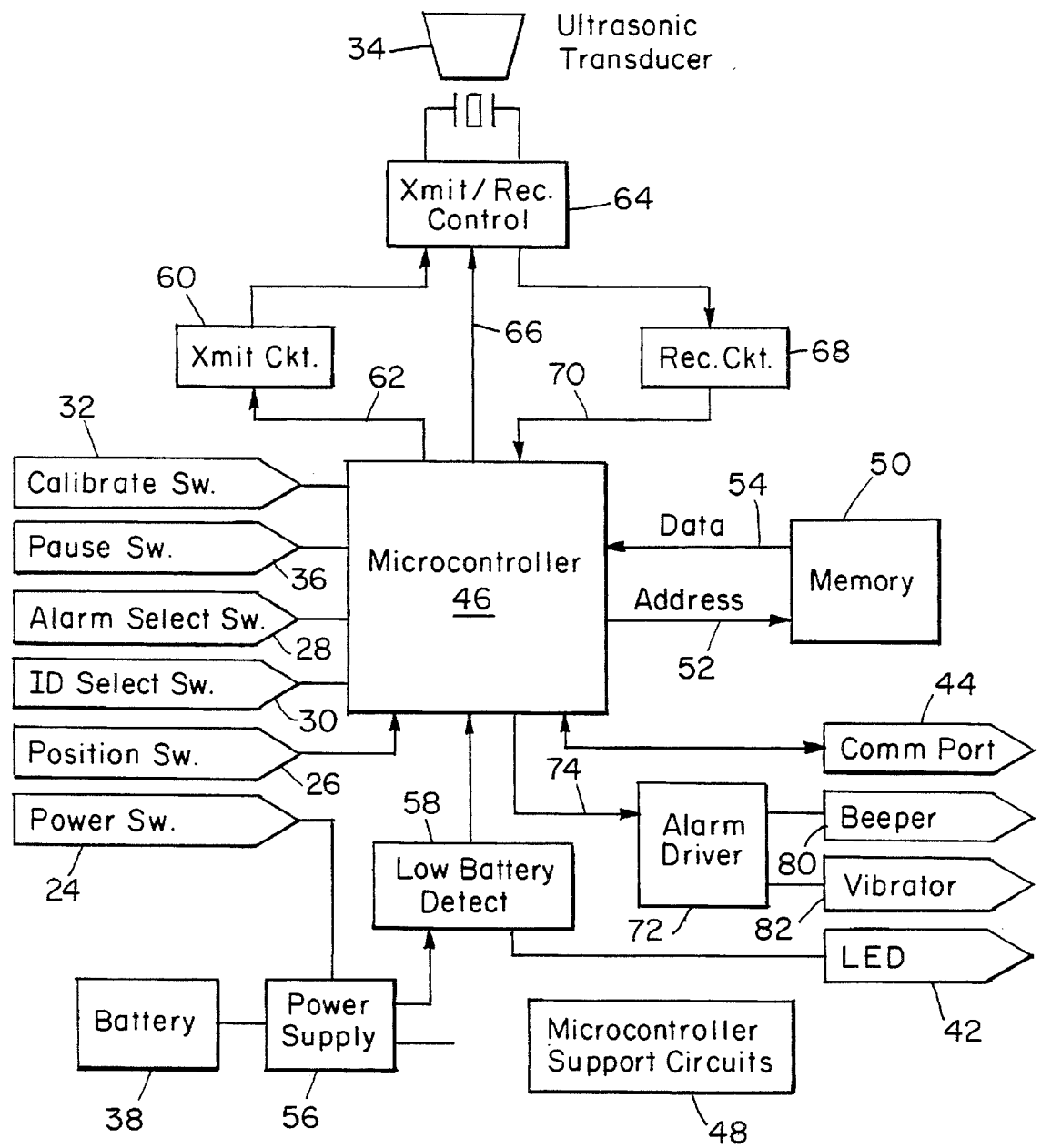
FIG. 3 is a block diagram of the electronics of the master unit of the preferred embodiment.

FIG. 3 is a block diagram of the master unit 12. During monitoring, the master unit 12 records in a memory 50 the number of minutes it has been operating and the number of alarms which have been issued during that time. The memory 50 can also record more detailed information such as the change in distance between units as a function of time. This information can be read by a peripheral device (not shown) via a serial interface at communication port 44.

One component of the master unit 12 is microcontroller 46. The microcontroller 46 can be of the Intel 8051 family or equivalent. The master unit 12 also comprises additional 8051 supporting logic integrated circuits 48. The microcontroller 46 receives inputs from the user and other sources and also controls the transmission/reception of ultrasonic signals and the other functions of the master unit 12.

The microcontroller 46 also interfaces with memory 50. This memory 50 may include random access memory (RAM), read only memory (ROM), and storage circuits internal to the microcontroller 46. The microcontroller 46 addresses data in the memory 50 by the well-known process of outputting an address to the memory 50 on an address bus 52 and reading corresponding data from a data bus 54. Among other things, the memory 50 stores calibration data used as threshold alarm trip points for standing and sitting positions. The memory 50 also stores the time of operation of the master unit 12 and the number of activations which have occurred during that time. This data, or other recordable data, can be read from the memory 50 by the microcontroller 46 and outputted to a peripheral device via the serial interface at the communication port 44.

To begin operation, the user activates power switch 24 to energize the master unit 12. Power from battery 38, regulated by power supply 56, is applied to the circuitry of the master unit 12. Low battery detect circuit 58 monitors the battery voltage. If the circuit 58 indicates that the voltage from power supply 56 is lower than a pre-determined minimum allowable level, the detect circuit 58 will activate the low batter indicator LED 42. In the master unit 12, battery power monitoring is performed by the low battery detect circuit 58 as shown. In the slave unit 18, battery power monitoring can be performed in the same way. In that case, a low battery indication may be encoded within the signal from the slave unit 18 to the master unit 12. In the preferred embodiment however, the receive circuit 68 (described below) in the master unit 12 monitors the power level of the signals from the slave unit 18. A low signal power level indicates a low battery 40 in the slave unit 18.

Before monitoring, the user calibrates the system to his own proper body positions. First, he selects the position he wishes to monitor, standing or sitting, via the position select switch 26. This input is read and stored by the microcontroller 46. Next, the user assumes a proper posture for the chosen position and presses and releases the calibrate switch 32. The microcontroller 46 reads the calibrate input. In response, it generates a series of logic pulses. The train of pulses is transmitted to transmit circuit 60 via line 62. The logic pulses are converted by the transmit circuit 60 to pulses capable of driving the ultrasonic transducer 34. The microcontroller 46 commands the transmit/receive control circuit 64 to the transmit mode via command line 66. This allows the transducer driver pulses from the transmit circuit 60 to pass through the transmit/receive control circuit 64 to the ultrasonic transducer 34. The pulses drive the transducer 34 and the desired ultrasonic signal is transmitted.

When the signal is transmitted, the microcontroller 46 starts a precision digital clock running. Then, the microcontroller commands the transmit/receive control circuit 64 to the receive mode via command line 66.

When the return signal from the slave unit 18 arrives at the master unit 12, it is received by the ultrasonic transducer 34. The signal passes through the transmit/receive control circuit 64 to the receive circuit 68. In the receive circuit 68, the signal is converted to a pulse which is compatible with the microcontroller 46. This pulse is transmitted to the microcontroller 46 over line 70.

When the microcontroller 46 detects the logic pulse from the receive circuit 68, it first checks the timer to determine if the reception time of the received signal is within an acceptable time window. If it is not, it is assumed that the received signal was not originally initiated by the master unit, and no further processing takes place. Thus, the precision clock provides a means for properly identifying signals associated with the master unit 12 and excluding signals from other units. If the reception time is within the acceptable time window, processing continues. The microcontroller 46 stops the precision clock. The time on the clock is the reference time to be used for further monitoring. This time is stored in memory 50 along with the position selected on the position select switch 26. Thus, if the user selected sitting on the position select switch 26 and then pressed the calibration switch 32, this time would be stored in memory 50 as the sitting position reference and would only be used during subsequent sitting posture monitoring.

After calibration is thus completed, monitoring can begin. During monitoring, the microcontroller 46 polls the position of the sample rate switch 30 and transmits a pulse to the slave unit 18. The microcontroller 46 starts the precision digital clock and reads and analyzes incoming pulses to determine if they correspond to transmitted pulses. When a received pulse is determined to be valid, the clock is stopped, and the time on the clock is compared to the stored reference time corresponding to the position setting of the position select switch 26. The absolute value of the difference between the two times corresponds to the amount that the distance between the units differs from that which existed during calibration. In a preferred embodiment, if this differential distance is greater than 0.25 inch in each of 3 consecutive samples, an alarm is issued. The microcontroller polls the alarm select switch 28 to determine which type of alarm, i.e., audible or vibrator, should be issued. It then commands the alarm driver 72 via command line 74 to drive the appropriate alarm device. If the audible alarm is selected, the alarm driver 72 drives the beeper 80. If the vibrator 82 is selected, the alarm driver 72 drives the vibrator 82.

Figure 4A:
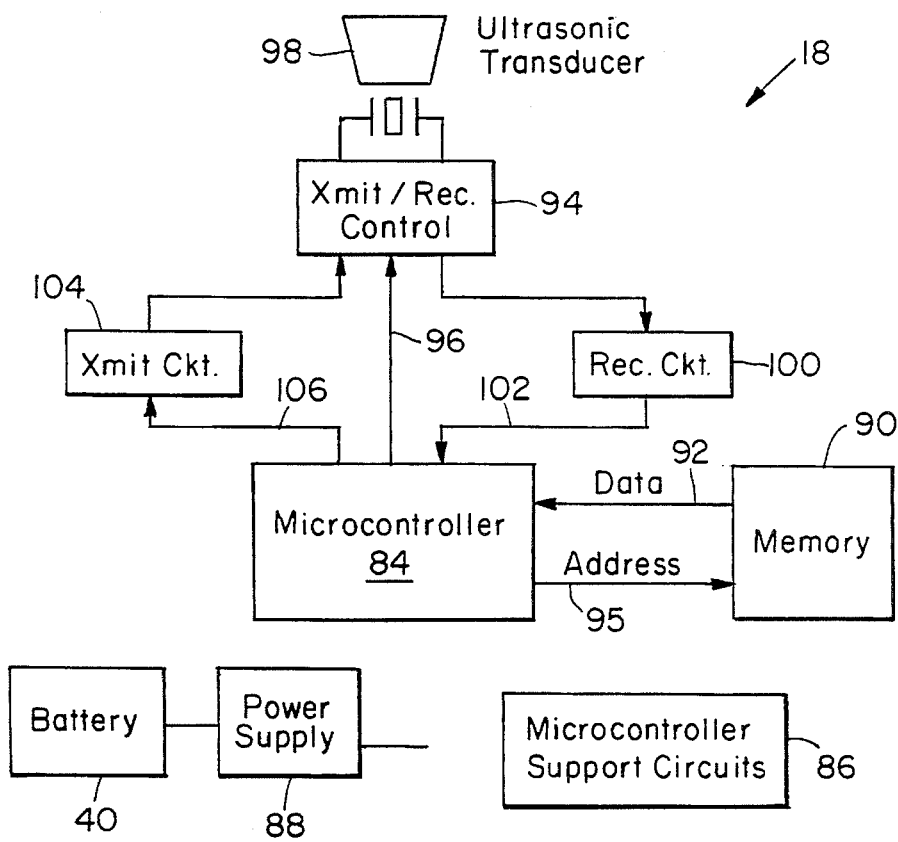
FIG. 4a is a block diagram of the electronics of one embodiment of the slave unit of the posture monitor.

FIG. 4a is a block diagram of one embodiment of the slave unit 18. Again, an Intel 8051 family or equivalent microcontroller 84, its support circuits 86 and memory 90 control the unit. The memory 90 transmits data on data bus 92 to the microcontroller 84 in response to a memory address being placed on address bus 95 by the microcontroller 84. The memory 90 may include RAM, ROM, and storage circuits internal to the microcontroller 84.

Power for the unit 18 is provided by battery 40. The battery power is regulated and applied to the circuitry in the unit 18 by power supply 88.

In a normal state, such as during monitoring, the microcontroller 84 commands the transmit/receive control circuit 94 to the receive mode via control line 96. A signal received by ultrasonic transducer 98 passes through transmit/receive control circuit 94 to receive circuit 100. The receive circuit 100 transforms the received pulsed signal into a chain of logic pulses by known means and transmits the pulses to the microcontroller 84 via line 102. The microcontroller 84 reads the pulses and formats a message for transmission to the master unit 12.

A chain of logic pulses is outputted to the transmit circuit 104 on line 106, and the transmit/receive control circuit 94 is commanded to the transmit mode via control line 96. The transmit circuit 104 converts the logic pulse chain to a pulse chain capable of driving ultrasonic transducer 98. These pulses pass through transmit/receive control circuit 94 and drive transducer 98 to transmit the pulsed ultrasonic signal to the master unit 12.

Figure 4B:
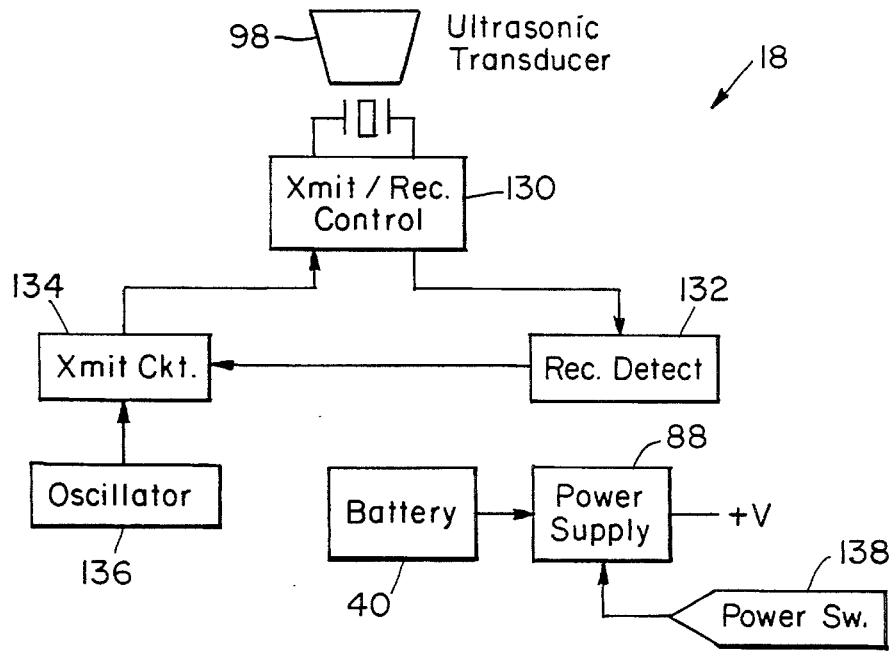
FIG. 4b is a block diagram of the electronics of another embodiment of the slave unit of the posture monitor.

FIG. 4b depicts a block diagram of another embodiment of the slave unit 18. Power is applied to the slave unit 18 upon activation of power switch 138. Power from battery 40 is regulated by power supply 88 and then applied to the slave unit electronics.

When monitoring begins, transmit/receive select circuit 130 is set to receive signals. The pulsed signal from the master unit 12 (not shown) is received by ultrasonic transducer 98 and passes through transmit/receive select circuit 130 to receive detect circuit 132. When the receive detect circuit 132 detects an incoming signal, it commands the transmit circuit 134 to transmit a signal back to the master unit 12. The transmit/receive select circuit 130 is commanded to the transmit mode. The oscillator 136 drives the transmit circuit 134 to transmit a signal through the transmit/receive select circuit 130 to the ultrasonic transducer 98 and on to the master unit 12.

Figure 5:
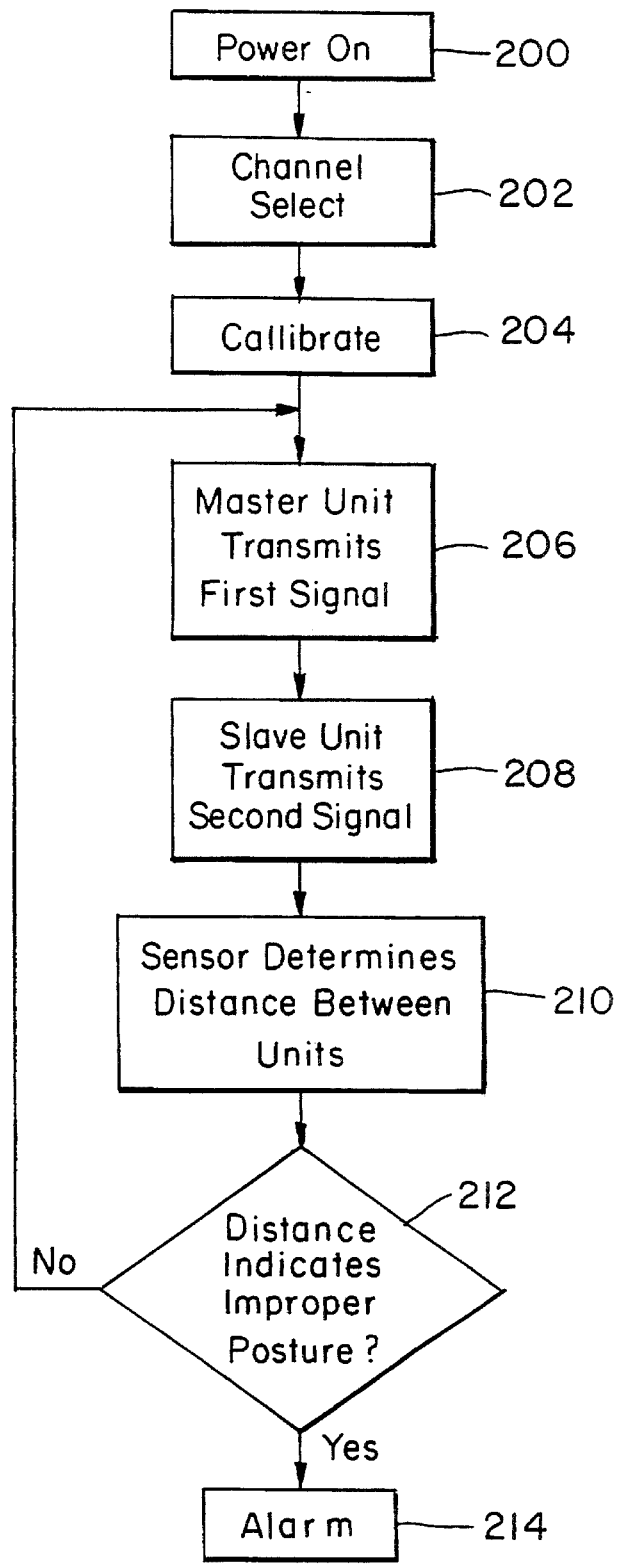
FIG. 5 illustrates the functional flow of a preferred embodiment of the present invention.

FIG. 5 illustrates the functional flow of a preferred embodiment of the present invention. In step 200, the user turns on the power. Next, the user selects a sample rate 202 to be used for the signals. Next, he calibrates 204 the monitor. In order to calibrate 204, he first assumes a proper sitting position and selects "sitting" on the position select switch 26 and presses the calibrate switch 32. Next, he stands in a proper position, changes the position select switch 26 to "standing" and presses the calibrate switch 32 again. This completes the calibration procedure 204.

After calibration 204, monitoring begins. First, the master unit 12 transmits a signal to the slave unit 18 as indicated in step 206. Upon receipt of the signal, the slave unit 18 transmits a signal to the master unit 12 as indicated in box 208. When the second signal arrives at the master unit 12, the time between transmission of the first signal and reception of the second signal is calculated in step 210. This time is compared to the ideal time set during calibration 204. A determination is made as to whether the distance between slave and master units varies from the ideal distance by more than the pre-set allowable amount as indicated in decision step 212. If it does not, normal monitoring continues. If it does, an error count is incremented in step 216. If the error count reaches three (decision block 218) before it is reset to zero in step 220, an alarm is initiated as indicated in step 214. In a preferred embodiment, this alarm may be delayed to allow the user to correct his posture on his own.

Other embodiments of the invention are possible. For example, the monitor 10 need not issue alarms to the user to indicate improper posture. The monitor 10 may simply record all of the posture data collected during a monitoring session in a memory 50. That data may be read from the monitor 10 via the communication port 44 or by other means.

Also, both units 12 and 18 need not contain transmit and receive circuitry. One of the units may simply reflect the signal transmitted by the other unit. In this embodiment, the first unit comprises an ultrasonic transducer 34 (see FIG. 2). It transmits a signal to the second unit and starts a timer. The signal reflects off a reflector which takes the place of the ultrasonic transducer 34 in the second unit and returns to the first unit. The first unit receives the signal via its transducer 34. The first unit then stops the timer and uses the measured time as discussed above to determine the distance between the units.

In other embodiments, one of the units comprises a transmitter and the other unit comprises a receiver. The units are synchronized. In one of these embodiments, the transmitter transmits a signal which is encoded with the time of the transmission. When the receiver receives the signal, it decodes the time and calculates the difference between that time and the time of reception. Thus, the distance between the units is indicated. In another of these embodiments, the transmitter transmits a signal of known power level. When the signal reaches the receiver in the other unit, its power level has been attenuated an amount which is dependent upon the distance between the units. The power level of the received signal is compared to a reference level set during calibration which is indicative of a proper distance.

Figure 6:
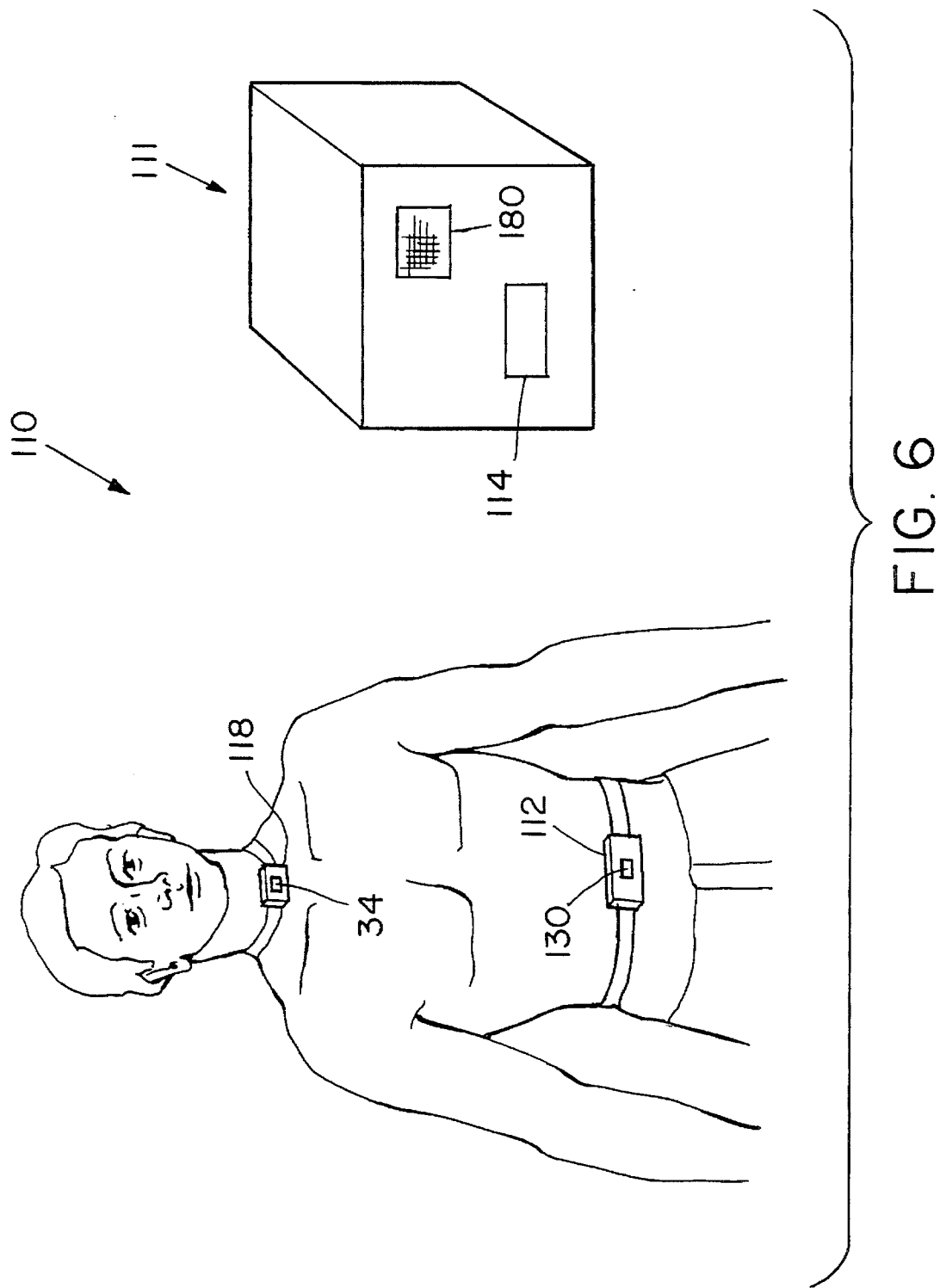
FIG. 6 is a view of a person with another embodiment of the posture monitor of the present invention attached to his body.

FIG. 6 schematically depicts an embodiment of the invention in which the monitor 110 comprises circuitry 111 external to the two units 112 and 118. Neck unit 118 comprises an ultrasonic transducer 34. Waist unit 112 comprises an ultrasonic transmitter 130. These units are chosen for illustration purposes only. It can also be the waist unit 112 which comprises the transducer 34 and the neck unit 118 which comprises the transmitter 130. Transmitter 130 transmits a signal to both the neck unit 118 and the external sensor circuitry 111. When the sensor circuitry 111 receives the signal via receiver 114, it starts a clock. When neck unit 118 receives the signal, it generates and transmits a second signal to the sensor circuitry 111. When the sensor circuitry 111 receives the second signal, it stops the clock. The time measured by the clock is indicative of the distance between the two units 112 and 118. If the measured distance indicates improper posture, alarm 180 sounds. Posture data may also be recorded.

These embodiments may also be realized with electric, magnetic, and electromagnetic signals. In these embodiments, the ultrasonic transmitters, receivers, and transducers are replaced with their appropriate counterparts and supporting circuitry well known in the art.

In the preferred embodiment, the dimensions of the master unit 12 are as follows:

Height: 1.1 in, max.
Width: 2.5 in, max.
Length: 3.9 in, max.

The dimensions of the slave unit are as follows:

Height: 0.660 in, max.
Weight: 1,100 in, max.
Length: 3,100 in, max.

While the preferred embodiment shows using ultrasonic signals, it will be understood that optical and electromagnetic or other signals can also be used. Also, the master unit can be located at positions other than the user's waist as can the slave unit. Alternatively, for example, the master unit can be fixed to the user's neck, and the slave unit can be fixed to the user's waist.

While this invention has been particularly shown and described with references to preferred embodiments thereof, it will be understood by those skilled in the art that various changes in form and details may be made therein without departing from the spirit and scope of the invention as defined by the appended claims.

We claim:

1. A posture monitoring system comprising:
   a first unit generating a first ultrasonic signal;
   a first mounting member for locating said first unit in substantially fixed relation to a first position on a user's body;
   a second unit, the first unit transmitting the first ultrasonic signal toward the second unit and the second unit returning a second ultrasonic signal to the first unit in response to the first ultrasonic signal; a second mounting member for locating said second unit in substantially fixed relation to a second position on the user's body at a distance from the first unit;
   a sensor in the first unit that senses the second ultrasonic signal to determine the distance between the first unit and the second unit;
   an alarm circuit in the first unit coupled to the sensor and having an alarm to communicate to the user a posture characteristic related to the distance between the first unit and the second unit: and
   a recorder circuit in the first unit storing posture data related to the distance between the first unit and second unit.

2. The posture monitoring system of claim 1 wherein one of the first position and second position is the user's neck, and the other position is the user's waist.

3. The posture monitoring system of claim 1 wherein the first position is the user's waist and the second position is the user's neck.

4. The posture monitoring system of claim 1 wherein the sensor comprises a microcontroller.

5. The posture monitoring system of claim 1 wherein the sensor uses the time of propagation of the first and second ultrasonic signals to sense the distance between the units.

6. The posture monitoring system of claim 1 further comprising:
   a first transmitter within the first unit that transmits the first ultrasonic signal to the second unit;
   a first receiver within the second unit that receives the first ultrasonic signal;
   a second transmitter within the second unit that transmits the second ultrasonic signal in response to the first ultrasonic signal;
   a second receiver within the first unit that receives the second ultrasonic signal; and
   a timer that measures the time between transmission of the first ultrasonic signal by the first transmitter and receipt of the second ultrasonic signal by the first receiver.

7. The posture monitoring system of claim 1 wherein the first ultrasonic signal is encoded with the time of transmission.

8. The posture monitoring system of claim 1 further comprising a position selector that adapts the posture monitoring system to monitor posture of the user in one of a plurality of positions of the user.

9. The posture monitoring system of claim 1 further comprising a calibrator that sets an initial distance between the first and second units indicative of proper posture of the user.

10. The posture monitoring system of claim 1 wherein the alarm comprises a vibrator.

11. The posture monitoring system of claim 1 further comprising delay circuitry that delays the alarm after improper posture is sensed.

12. The posture monitoring system of claim 1 further comprising pausing circuitry that inhibits the alarm.

13. The posture monitoring system of claim 1 further comprising a data communication port in the first unit that couples the monitoring system to communicate the posture first unit to a peripheral device.

14. The posture monitoring system of claim 1 wherein the alarm is audible.

15. A posture monitoring system comprising:
   first unit comprising a first transmitter that generates a first ultrasonic signal and a first receiver that detects a second ultrasonic signal; a first mounting ember for locating said first unit in substantially fixed relation to a first position on a user's body; second unit comprising a second transmitter that transmits the second ultrasonic signal and a second receiver that detects the first ultrasonic signal, the second transmitter transmitting the second ultrasonic signal in response to the second receiver detecting the first ultrasonic signal; a second mounting member for locating said second unit in substantially fixed relation to a second position on the user's body at a distance from the first unit;
   a sensor in the first unit that senses the time between transmission of the first ultrasonic signal and reception of the second ultrasonic signal at the first unit to determine the distance between the first unit and second unit; and
   an alarm circuit in the first unit having an alarm to communicate to the user a posture characteristic related to the distance between the first and second units.

16. A posture monitoring system comprising:
   first unit having a first transmitter that transmits a first ultrasonic signal and a first receiver that detects a second ultrasonic signal; a first mounting member for locating said first unit in substantially fixed relation to a first position on a user's body;
   second unit having a second transmitter that transmits the second ultrasonic signal and a second receiver that detects the first ultrasonic signal, the second transmitter transmitting the second ultrasonic signal in response to the detected first ultrasonic signal; a second mounting member for locating said second unit in substantially fixed relation to a second position on the user's body at a distance from the first unit;

a sensor in the first unit that senses the time between transmission of the first ultrasonic signal and reception of the second ultrasonic signal at the first unit to determine the distance between the first unit and the second unit; and a recorder circuit that stores posture data related to the distance between the first and second units.

17. A posture monitoring system comprising:

first unit having a first transmitter that transmits a first ultrasonic signal and a first receiver that receives a second ultrasonic signal; a first mounting member for locating said first unit in substantially fixed relation to a first position on a user's body; second unit comprising a second transmitter that transmits the second ultrasonic signal and a second receiver that receives the first ultrasonic signal, the second transmitter transmitting the second ultrasonic signal in response to the second receiver receiving the first ultrasonic signal; a second mounting member for locating said second unit in substantially fixed relation to a second position on the user's body at a distance from the first unit;

a sensor in the first unit that senses the time between transmission of the first ultrasonic signal and reception of the second ultrasonic signal at the first unit to determine the distance between the first unit and the second unit;

an alarm circuit in the first unit having an alarm to communicate to the user a posture characteristic related to the distance between the first and second units a recorder circuit in the first unit that stores posture data related to the distance between the first and second units; and a data communication port in the first unit that couples the first unit to a peripheral device.

18. A posture monitoring system comprising:

a first unit comprising a first transmitter that transmits a first ultrasonic signal and a first receiver that receives a second ultrasonic signal; a first mounting member for locating said first unit in substantially fixed relation to a first position on a user's body;

a second unit comprising a second transmitter that transmits the second ultrasonic signal and a second receiver that receives the first ultrasonic signal, the second transmitter transmitting the second ultrasonic signal in response to the second receiver receiving the first ultrasonic signal; a second mounting member for locating said second unit in substantially fixed relation to a second position on the user's body at a distance from the first unit;

a sensor in the first unit that senses the time between transmission of the first ultrasonic signal and reception of the second ultrasonic signal at the first unit to determine the distance between the first unit and the second unit; and a communication port in the first unit that provides posture data related to the distance between the first and second units from the first unit to a peripheral device.

* * * * *